United States Patent [19]

Ayoub

[11] Patent Number: 4,689,230
[45] Date of Patent: Aug. 25, 1987

[54] CONTRACEPTIVE COMPOSITION FOR EXTERNAL APPLICATION

[75] Inventor: Nabeel H. Ayoub, Overbrook, Pa.

[73] Assignee: John B. Sowell, Ardmore, Pa.

[21] Appl. No.: 561,527

[22] Filed: Dec. 15, 1983

Related U.S. Application Data

[63] Continuation-in-part of Ser. No. 191,865, Feb. 29, 1980, abandoned.

[51] Int. Cl.$^4$ .............................................. A61K 35/78
[52] U.S. Cl. ...................... 424/195.1; 424/DIG. 14; 514/843; 514/899; 514/936
[58] Field of Search ............ 424/195, 195.1, DIG. 14; 514/843, 899, 936

[56] References Cited

U.S. PATENT DOCUMENTS

| | | | |
|---|---|---|---|
| 104,094 | 6/1870 | Woolrich | 424/195 |
| 194,379 | 8/1877 | Shoenfeld | 424/195 |
| 196,916 | 11/1877 | Marshall | 424/195 |
| 207,474 | 8/1878 | Anderson | 424/195 |
| 302,761 | 7/1884 | Moore | 424/195 |

Primary Examiner—Johnnie R. Brown
Assistant Examiner—John W. Rollins, Jr.
Attorney, Agent, or Firm—John B. Sowell

[57] ABSTRACT

Plant extracts are employed to provide a menses inducing composition for topical application. Common commercially available fenugreek seeds and commercially available ginger are mixed in a preferred range of ratios and combined in a dry powder form for topical application to the outside of the abdomen of the female to induce menses.

19 Claims, 4 Drawing Figures

CONTRACEPTIVE COMPOSITION FOR EXTERNAL APPLICATION

RELATED APPLICATIONS

This is a continuation in part of application Ser. No. 191,865 filed Feb. 29, 1980, now abandoned.

BACKGROUND OF THE INVENTION

1. Field of the Invention

The present invention relates to female contraceptives and more particularly to a menses inducing plant extract composition prepared for topical or external application.

2. Description of the Prior Art

Pharmaceutical compositions obtained from plants and plant extracts are well known and are classified in U.S. Class 424, subclass 195 (International Class A61K 35/78).

Plant extract compositions for controlling fertility in female mammals are known. U.S. Pat. No. 4,006,227 disclosed an extract obtained from Montanoa tomentosa administered internally to induce menses. This reference also discusses employing the extract to induce labor and delivery of newborn mammals. The extract, when properly administered, reduced blood levels of progesterone.

U.S. Pat. No. 4,148,892 discloses a plant extract male contraceptive composition obtained from Ecballium elaterium, Linn, prepared in solution form for oral internal administration. The extract when properly administered inhibits the male sperm's activity.

Some known oral birth control pills employ natural or synthetic hormonal compounds which inhibit ovulation and discourages the uterine lining from accepting a fertilized egg. The hormones such as testerone and estradiol and other forms of estrogen are responsible for the pills known side effects.

It is well known that commercially available foam, jellies, creams and suppositories are available for female contraceptives. Such devices and compositions are intended for application inside the body and are designed to inhibit the male sperm's activity. These compositions are generally referred to as spermicides. The VLI Corporation has developed a contraceptive sponge containing spermicide which is applied inside the body.

Orally administered female contraceptives utilizing synthetic progestational and estrogenic substances inhibit follicle stimulated hormone (FSH) and leteinizing hormone (LH) to prevent ovulation.

Other types of birth control devices have been tried and as yet none meet the requirement of avoiding all types of side effects while providing substantially infallible protection.

Before this invention was made, one of the ingredients, fenugreek seed, had been taken orally in herbal tea for colds and general health inducement. When taken orally in large amounts fenugreek tea causes upset stomach. The other ingredient, ginger, is universally used as a flavor for pastries and food. Ginger is also used to flavor tea, however, excessive amounts induce upset stomach. It is also known that fenugreek seeds have been employed for condiment and medicinal uses. (See "Garden Spice and Wild Pot-Herbs") by Muenscher et al Cornell University Press, Ithaca, N. Y. 1955)

There is, and there has been, a long unfulfilled need for any form of female contraceptive which would prevent pregnancy effectively and without side effects.

SUMMARY OF THE INVENTION

The present invention provides a simple and reliable means for inducing menses without side effects.

It is the primary object of the present invention to provide a herbal formula for topical application as an effective menses inducing means.

It is another primary object of the present invention to provide a new topical contraceptive for external application.

It is another object of the present invention to provide an herbal composition to induce menses by providing the zygot from forming in the uterus.

It is another object of the present invention to provide a menses inducing composition for creating an unstable condition which causes the placenta to collapse.

It is another object of the present invention to provide an herbal composition for inducing menses by external application and enhanced by the addition of a penetrating agent.

It is another object of the present invention to provide a pungent herbal composition for inducing menses by external application and added thereto a masking agent with aromatic qualities for masking the pungent odor.

It is yet another object to provide a bandage-like container for maintaining the herbal composition in dispersed form.

It is another object to provide a retainer for use in conjunction with the bandage-like container.

According to these and other objects of the present invention there is provided an herbal composition of substantially equal parts of ground or powdered fenugreek seed and giner placed between two layers of porous material and having a non-porous outer backing layer which is placed as a laminar structure over the naval and stomach area of a female to induce menses by external (topical) application to permit penetration of the pharmacological agents through the skin into the blood stream.

DESCRIPTION OF THE PREFERRED EMBODIMENT

Figure 1:
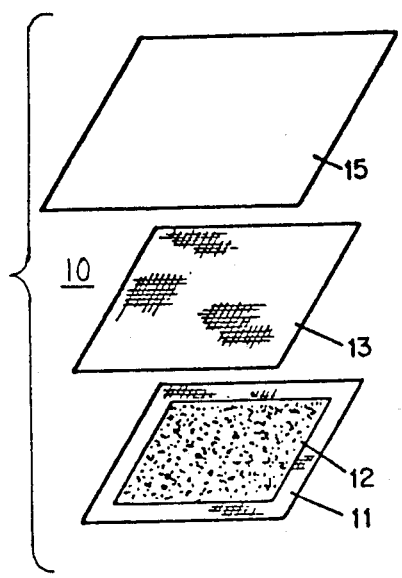
FIG. 1 is an exploded isometric view showing a preferred embodiment dry poultice for external application.

Before explaining the preferred embodiment, it should be noted that several worldwide agencies have been actively seeking a male or female contraceptive possessing the qualities of simplicity, acceptability, efficacy, nontoxicity and the absence of adverse side effects. As described in U.S. Pat. No. 4,148,892 the compound or apparatus must be usable in a form which requires no training for use by basically illiterate people.

The three active ingredients employed in the present invention are Trigonelline, Zingerone and Shogaol. Trigonelline is found in the plant *Trigonella foenumgraeium* of the family Leguminosae. Trigonella or Greek Hay Seed is commonly called fenugreek. This annual herb is common to Europe, Northern Africa and India. The seeds of this plant contain the alkaloid trigonelline which is also found in hempseed, peas, oats and other seeds and has been identified as the methybetaine of nicotine acid. Trigonelline has the chemical composition $C_7H_7NO_2$. Fenugreek seed is known to comprise approximately 0.13% trigonelline by weight.

Zingerone is found in the plant family Zingirberaceae or Zingiber, commonly known as ginger. The root or rhizone of this plant family includes seventy species of perennial ginger herbs. The most common form of this plant is called Jamacian or African ginger. Ginger can be commercially obtained in black, green or white forms already ground. This family of plants are found worldwide. The dried root or rhizone yields commercial ginger which contains zigerone identified as 4-hydroxy-5 methoxy-phenylethyl-methyl ketone. Its chemical composition is $C_{11}H_{14}O_3$ and forms a crystalline solid.

Shogaol is also found in Zingiber and can be obtained from common ginger. This ingredient is an unsaturated ketone, homologous with zingerone and has the chemical formula $C_{17}H_{24}O_3$. Commercially available ground ginger contains the active ingredients Shogoal and Zingeron in the proper theraputic amounts.

When the phrase "induce menses" is used hereinafter it will be understood to mean female homo sapians even though the same ingredients would be applicable to other primates. Test and examples are present herein.

The contraceptive composition has been prepared by making a dry powder of fenugreek seeds to the consistency of baking flour. Dry black ginger obtained in powdered form was employed which was already prepared for commercial use as a very fine powder intended for human consumption in confections and teas. Grinding with a mortar and pestle will produce a desirable very fine powder mixture.

A preferred mixture of the dry ingredients is one to one by weight of powdered ginger and powdered fenugreek seeds. Variations of the novel mixture have been found to be possible wherein up to ten percent more ginger than fenugreek seeds makes little change in the effectiveness. Conversely, as much as up to thirty percent more fenugreek seeds than ginger by weight has found to be very effective. The dry mixture once prepared may be topically applied in dry, paste or ointment or salve form as will be explained.

The range in which results have been obtained extends beyond the preferred range of one to one. It has been found that two to eight grams of fenugreek mixed with two to eight grams of ginger so that the total weight of the composition is in the area of ten grams, plus or minus two grams, provides an effective mixture even though not a preferred mixture.

An average weight American female of medium frame has a body weight between 110 and 150 pounds or 50 to 68 kilograms. A mixture of five grams of the composition provides 0.1 to 0.074 grams per kilogram of body weight whereas a mixture of ten grams provides 0.2 to 0.147 grams per kilogram of body weight. The effective mixture of eight to twelve grams (0.24 gram per kilogram) of mixture will preferably be reduced to the smallest effective total weight of mixture or its equivalent of the active ingredients discussed hereinbefore. The theraputic amount of active ingredients found in three to five grams of fenugreek seeds is only about 390 to 650 miligrams of trigonelline and has been found to be effective. Zingerone has been isolated from ginger in combination with other elements and forms less than 1000 miligrams of the active ingredients in three to five grams of ginger. Shogaol has not only been isolated from ginger but its synthesis has been worked out and forms even less by weight than Zingerone.

After the dried powdered mixture is prepared and before being applied to a dry poultice, a penetrating agent such as dimethyl sulfoxide (DMSO) may be added to enhance the penetrating qualities of the mixture by adding up to ten percent by weight to the powdered mixture. Other compositions which enhance penetration of pharmacologically active agents through the skin are described in U.S. Pat. No. 4,148,893 and the art cited therein. Up to ten percent weight of liquid can be absorbed by the mixture without forming a wet paste.

Refer now to FIG. 1 showing a preferred embodiment dry external poultice or pad 10. The pad 10 comprises an inside layer of porous cloth 11 such as cheese cloth or gauze onto which a preferred amount of novel mixture 12 has been applied. It will be understood that the mixture does not entirely cover the inside porous cloth 11 and a border of up to one inch at the edges of the cloth 11 is desirable for purposes which will be explained. A cover cloth 13 which may be a different cloth or the same cloth as layer 11 is applied over the mixture and the inside porous cloth 11 and is preferably attached thereto by stitching the edges around the mixture and also performing a random stitch throughout the center area to prevent the mixture from shifting. Layer 15 is a non-porous outside layer and in the preferred embodiment is made from household adhesive tape. The outside area of the non-porous layer 15 is larger than layer 13 which is the same size as layer 11 and provides means for attaching the dry poultice to the human body. It will be understood that the adhesive tape adheres to the top of layer 13 and has free adhesive areas at the edges for attachment to the human body which may have a removable protective layer before attachment.

The shape of the dry poultice 10 is designed for topical application attachment to the human body at an area over the navel and/or over the uterus area. The area of the active ingredient mixture is preferably approximately nine square inches and contains nine to ten grams of the novel mixture. The size of the poultice and the amount of the mixture may be made larger for larger humans and the size of the poultice may be scaled down for smaller humans. When the poultice 10 is designed to fit into the navel cavity the area covered is much smaller in area.

Figure 2:
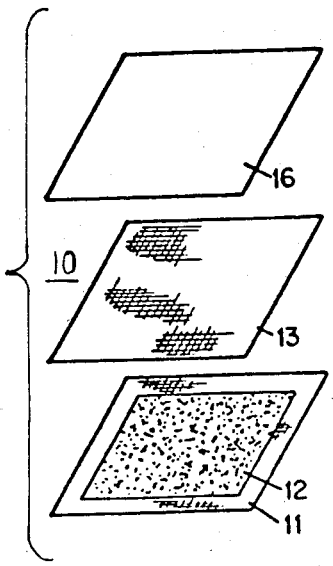
FIG. 2 is an exploded isometric view of a modification of FIG. 1.

Refer to FIG. 2 showing a modified embodiment of FIG. 1. The inside porous layer 11, the dry mixture 12 and the cover cloth 13 are the same as employed in the FIG. 1 structure. However, instead of adhesive tape 15 there is applied by stitching to the aforementioned three layers a non-porous plastic outer layer 16. In this example the dry poultice is intended to be inserted inside of a high waist girdle or women's under garment apparel which will maintain the inside cloth layer 11 in substantial contact with the body over the navel and uterus area. Since there are numerous ways for applying such a dry poultice to the human body area to maintain continuous contact, further explanation and examples are not required herein. The dry poultice merely provides a preferred way to apply the novel mixture which contains the active ingredients.

Figure 3:
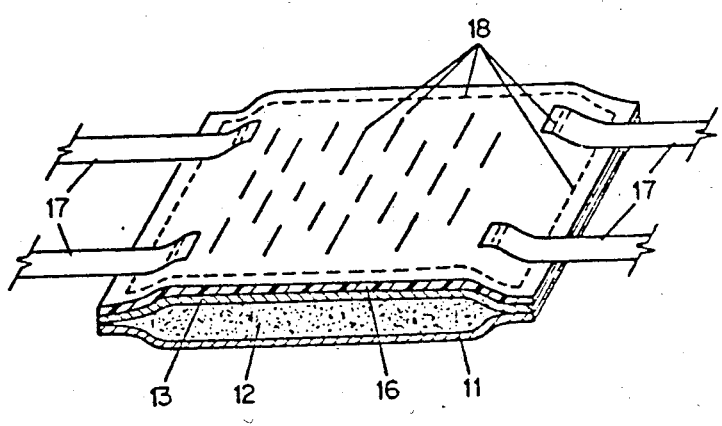
FIG. 3 is an end view isometric of a modification of FIG. 2.

Refer to FIG. 3 which shows in exaggerated form an end view of the dry poultice in isometric form. FIG. 3 is a modified form of FIG. 2 and the afore-mentioned layers 11, 12, 13 and 16 are the same as those explained with regard to FIG. 2. Four body ties 17 are shown attached to the top of the plastic layer 16 by stitches 13 which are employed to hold the poultice together. It will be understood that strips of adhesive tape similar to the ties 7 could be employed to attach the dry poultice to the human body for topical application in the preferred manner explained hereinbefore.

Figure 4:
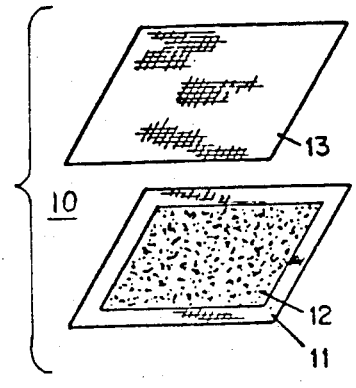
FIG. 4 is an exploded isometric view of a commercially desirable marketable form of the present invention.

FIG. 4 is a simplified form of the invention explained hereinbefore with regards to FIGS. 1 through 3. The layers 11, 12 and 13 are preferably identical to the aforementioned described layers with regards to FIGS. 1 through 3. It will be understood that the cover layer 13 is a cloth layer and is porous in this example. In order to use this poultice in a preferred environment the poultice should be held in place by a high waist rubber corset of the type used for weight reduction and trimming the waist. Thus, the use of the commercially desirable and marketable form shown in FIG. 4 requires the use of some outer non-porous layer to hold in the moisture which seeps from the body after application. An adhesive tape layer 15 as employed in FIG. 1 can be used to cover the active ingredients when concentrated in a small ball or button form.

The poultice 10 is applied dry and can be left on for a period of two weeks. The embodiment of FIG. 1 may be left on in the shower, however, the other forms explained hereinbefore can be removed temporarily for bathing, unless covered with adhesive tape.

When the mixture is only separated from the skin by a porous layer 11, the active ingredients of the mixture penetrate into the skin and the body. The body moisture under the dry poultice is trapped in the poultice and behind the outer nonporous layers 15 or 16 as the case may be and the addition of body moisture enhances the penetration of the active ingredients into the skin.

Studies have shown that the active ingredients start to penetrate the human body within a short period of time and it is known that the novel ingredients have been effective to induce menses within twenty-four to forty-eight hours in the human body.

While the action effected by the active ingredients is not fully understood, it is presumed from tests and observations that the active ingredients when applied at or before the mid-point of the menstrual cycle cause the sperm to be unstable so as to prevent conception.

When the invention is applied at or near the beginning of the menstrual cycle, the active ingredients create a highly unstable state which causes the placenta to collapse and induce menses.

EXAMPLE 1

The user was known to have erratic cycles. The mixture of powdered fenugreek seed and ginger was employed to adjust the cycle to approximately thirty days by applying topically the invention approximately three days before the preferred start of the cycle time. Menses was induced within one to three days after application and resulted in a regular and established thirty day cycle.

EXAMPLE 2

The user was known to have regular cycles. The mixture of powdered fenugreek seed and ginger was applied on three separate occasions at or shortly after the end of the expected cycle to induce menses, which was induced promptly each time within two days of the time of topical application.

EXAMPLE 3

The user in this case did not have confirmation of conception, but was one week beyond the expected start of a cycle. Topical application of powdered fenugreek seed and ginger induced menses within three days.

EXAMPLE 4

A test primate was confirmed to be pregnant. Application of the invention shortly after confirmation of pregnancy induced menses within five days.

Having explained the preferred embodiments of the present invention with the aforementioned examples it will be understood that there was no toxic element involved and there were no side effects observed. The users referred to in the above examples suffered no inconvenience during the application of the invention.

Having explained a preferred embodiment of the invention and modifications of the use of the novel composition of herbal ingredients it will be understood that other additives which are not to be considered active ingredients may be employed. For example, ginger has a pungent odor. To mask the effect of the odor of ginger and to some extent the odor of fenugreek a masking agent can be employed to shield, hide or mask the odor. Effective masking agents and perfumes are well known and do not require further elaboration herein. K-Y jelly and other salves may be employed to form a pastelike composition to enhance the mixture to skin contact required for topical applications.

Having explained the preferred herbs and having identified the active ingredients employed in the present invention it will be understood that other forms of herbs having the same active ingredients may be employed to achieve the same outstanding results described hereinbefore. Further, the active ingredient of the herbs and reasonable substitutes therefor may be synthetically reproduced and employed as a substitute for the plant extract compositions.

It will be understood that the embodiments shown in the drawings are the preferred embodiments and that changes could be made by adding or subtracting layers. For example, the active ingredients could be applied directly to the body mixed with a salve carrier or to an adhesive porous or non-porous outer layer and could be adhesively attached to the body, however, such embodiments are not as convenient or effective as the preferred embodiments.

I claim:

1. A composition for topical application in dry form adapted for application to human females against the navel and stomach area to promote the menstrual cycle consisting essentially of: a therapeutic amount of powdered fenugreek seeds and powdered ginger comprising approximately one part of powdered fenugreek seeds and one part powdered ginger.

2. A composition for topical application as set forth in claim 1 wherein the active ingredients in therapeutic amount comprise Trigonelline in said powdered fenugreek seeds and Zigerone and Shogaol in said powdered ginger.

3. A composition for topical application as set forth in claim 2 which further includes a penetration agent for enhancing penetration of said active ingredients through the skin.

4. A composition for topical application as set forth in claim 3 wherein said penetration agent comprises Dimethyl sulfoxide (DMSO).

5. A composition for topical application as set forth in claim 4 wherein said DMSO comprises less than ten percent by weight.

6. A composition for topical application as set forth in claim 4 wherein said DMSO is in liquid form and the amount employed in said composition does not completely wet said composition to form a paste.

7. A composition for topical application as set forth in claim 1 comprising three to five grams of powdered fenugreek seeds and two to five grams of powdered ginger.

8. A composition for topical application as set forth in claim 7 wherein an effective amount of composition comprises a total weight of six to ten grams.

9. A composition for topical application as set forth in claim 1 wherein the moisture content of said composition does not exceed ten percent.

10. A composition for topical application as set forth in claim 1 which further includes a salve forming a paste like carrier for said composition.

11. A composition for topical application as set forth in claim 10 wherein said salve comprises surgical jelly.

12. A composition for topical application in dry form adapted for application to human females against the navel and stomach area to promote the menstrual cycle consisting essentially of from two to eight grams of dry powdered fenugreek seeds, and from two to eight grams of dry powdered ginger.

13. A composition for topical application adapted for application to human females against the navel and stomach area to promote the menstrual cycle consisting essentially of: a therapeutic amount of powdered fenugreek seeds and powdered ginger comprising approximately one part of powdered fenugreek seeds and one part of powdered ginger, said composition being in dry poultice form.

14. The composition for topical application as set forth in claim 13 wherein said poultice comprises a non-porous backing covering a porous cloth retainer.

15. The composition for topical application as set forth in claim 14 wherein said nonporous backing is provided with adhesive for holding said cloth and said composition thereto.

16. A method for inducing menses in adult females by the topical administration of an effective amount of a menses-inducing composition comprising the steps of:
preparing a menses inducing composition consisting essentially of fenugreek seeds in dry powdered form mixed with ginger in dry powdered form,
placing powdered composition between two layers of porous material,
placing a non-porous backing over an outer layer of said porous material, and applying the inner porous layer of material against the stomach at the navel area.

17. A method for inducing menses as set forth in claim 16 wherein the step of placing the composition ingredients between two layer of porous material comprises the steps of spreading said ingredients over a piece of porous cloth,
applying a second porous cloth over the ingredients to hold the ingredients in place, and
physically attaching said porous layers together to entrap said ingredients therebetween.

18. A method for inducing menses as set forth in claim 17 which further includes the step of providing means for holding said non-porous backing layer to one of said porous layers.

19. A method for inducing menses as set forth in claim 18 which further includes the step of providing means for holding said outer porous layer of material against the stomach.

* * * * *